(12) United States Patent
Takata

(10) Patent No.: US 11,227,062 B2
(45) Date of Patent: Jan. 18, 2022

(54) DATA MANAGEMENT METHOD, APPARATUS AND SYSTEM FOR MACHINE LEARNING SYSTEM

(71) Applicant: Hitachi, Ltd., Tokyo (JP)

(72) Inventor: Mika Takata, San Jose, CA (US)

(73) Assignee: HITACHI, LTD., Tokyo (JP)

( * ) Notice: Subject to any disclaimer, the term of this patent is extended or adjusted under 35 U.S.C. 154(b) by 196 days.

(21) Appl. No.: 16/503,334

(22) Filed: Jul. 3, 2019

(65) Prior Publication Data

US 2021/0004480 A1   Jan. 7, 2021

(51) Int. Cl.
  *G06F 21/62* (2013.01)
  *G16H 10/60* (2018.01)
  *G16H 50/70* (2018.01)
  *G06N 20/00* (2019.01)

(52) U.S. Cl.
  CPC ......... *G06F 21/6245* (2013.01); *G06N 20/00* (2019.01); *G16H 10/60* (2018.01); *G16H 50/70* (2018.01)

(58) Field of Classification Search
  CPC . G06F 21/6245; G06F 21/6254; G16H 10/60; G16H 20/00; G01H 50/70
  See application file for complete search history.

(56) References Cited

U.S. PATENT DOCUMENTS

| | | | | |
|---|---|---|---|---|
| 2013/0085773 A1* | 4/2013 | Yao | ........................ | G06Q 10/04 705/2 |
| 2016/0364544 A1* | 12/2016 | Das | ........................ | G16H 50/20 |
| 2017/0083926 A1* | 3/2017 | Karcher | ............. | G06Q 30/0201 |
| 2017/0357760 A1* | 12/2017 | Han | ........................ | G06N 20/20 |
| 2018/0314939 A1* | 11/2018 | Skiles | ...................... | G06N 3/08 |
| 2020/0335225 A1* | 10/2020 | Quintero Padron | ... | G16H 50/70 |

OTHER PUBLICATIONS

Guyon, I. et al. "An Introduction to Variable and Feature Selection" Journal of Machine Learning Research 3 (2003) pp. 1157-1182 (26 pages).

(Continued)

*Primary Examiner* — Tongoc Tran
(74) *Attorney, Agent, or Firm* — Procopio, Cory, Hargreaves & Savitch, LLP

(57) ABSTRACT

Example implementations described herein are directed to systems and methods for selecting appropriate data samples and features in an access and privacy restricted system. Example implementations involve selection of appropriate samples (e.g. patients) which have enough data sources bringing highly important factors based on the experienced risk factors at other facilities, which is stored as metadata. The risk factor management puts more prioritization on some patients which have more data in the required data source than the other patients among all data sample candidates. The similarity of the training data sample can be a criteria to select new sample sets. Further, the risk factor management selects valuable features effectively based on metadata derived from other facilities. Example implementations help improve machine learning accuracy as part of daily system management in a facility, and can be deployed across facilities without compromising access or privacy restrictions of the data.

15 Claims, 23 Drawing Sheets

(56) References Cited

OTHER PUBLICATIONS

Miao, H. et al. "ModelHub: Lifecycle Management for Deep Learning" University of Maryland: CMSC 396H: Undergraduate Honors Seminar (4 pages).
Pan, S. et al. "A Survey on Transfer Learning" IEEE Transactions on Knowledge and Data Engineering (15 pages).
Brown, G. "Ensemble Learning" Encyclopedia of Machine Learning, 2010, Springer, Boston, MA (7 pages) resubmission of NPL with eligible text for IDS from Jul. 3, 2019.
Vartak, M. et al. "ModelDB: A System for Managing Machine Learning Models" Intel Science and Technology Center for Big Data, May 25, 2016 (3 pages) resubmission of NPL with eligible text for IDS from Jul. 3, 2019.

\* cited by examiner

FIG. 9

TestMETA

| Name | Type |
|---|---|
| MODEL_ID | int |
| FEATURES_ID | int |
| TEST_PATIENT_ID | String |
| TEST_RESULT | JSON |
| TIME_STAMP | Timestamp |

ModelMETA

| Name | Type |
|---|---|
| MODEL_ID | int |
| FEATURES_ID | int |
| ALGORITHM | String |
| TUNING_PARAM | JSON |
| VALIDATION | JSON |
| MODEL_PATH | string |
| TIME_STAMP | Timestamp |

FeaturesMETA

| Name | Type |
|---|---|
| FEATURES_ID | int |
| FEATURES_LINEAGE (e.g Features file) | String |
| NUM_OF_SAMPLES | Int |
| RECIPE | String |
| TIME_STAMP | Timestamp |

FeaturesELEMENT

| Name | Type |
|---|---|
| FEATURES_ELEMENT_ID | int |
| FEATURES_ID | int |
| FEATURES_ELEMENT_NAME | String |
| FEATURES_ELEMENT_LINEAGE (pointer to DWH column/table) | String |
| DATASOURCE_ID | String |
| OPERATOR_PATH (e.g kl) | String |
| TIME_STAMP | Timestamp |

DatasourceELEMENT

| Name | Type | |
|---|---|---|
| DATASOURCE_ID | int | ** |
| DATASOURCE | String | |
| VALID_START_DATE | Date | * |
| VALID_END_DATE | Date | * |
| TIME_STAMP | Timestamp | |

| Prediction result_id | Model_ID | Features_ID | Test_Patient_ID | Readmission_Prediction_result |
|---|---|---|---|---|
| 1 | 1 | 100 | 1000 | 0.7 |
| 2 | 1 | 100 | 1001 | 0.3 |
| 3 | 1 | 100 | 1002 | 0.5 |
| 4 | 1 | 100 | 1003 | 0.6 |
| 5 | 1 | 100 | 1004 | 0.8 |
| 6 | 1 | 100 | ••• | •• |
| 7 | 1 | 100 | 2000 | 0.1 |

FIG. 10

| Prediction_result_ID | Feature_element_id | Importance_value |
|---|---|---|
| 1 | 3001 | 0.89 |
| 1 | 2499 | 0.67 |
| 1 | 2922 | 0.64 |
| 1 | 101 | 0.37 |
| 1 | 2900 | 0.22 |
| 1 | ••• | ••• |
| 2 | 3000 | 0.82 |

FIG. 11

| Features_ID | Features_element_id | Label |
|---|---|---|
| 1 | 1 | 1 |
| 1 | 2 | 1 |
| 1 | 3 | 0 |
| 1 | 4 | 1 |
| 1 | 5 | 1 |
| 1 | 6 | 0 |
| 1 | 7 | 0 |

FIG. 12

| Patient_ID | Index_Patient_Key | Lab_test_A | Frequency of med_B | ... |
|---|---|---|---|---|
| 1 | P00001_0000 | 0.2 | 0.32 | ... |
| 1 | P00001_0001 | 0.3 | 0.44 | ... |
| 2 | P00002_0000 | 0.1 | 0.3 | ... |
| 2 | P00002_0001 | 0.5 | 0.2 | ... |
| 2 | P00002_0002 | 0.46 | 0.15 | ... |
| 3 | P00003_0000 | 0.43 | 0.4 | ... |

FIG. 13

| Patient ID | Data selection priority |
|---|---|
| N00001 | 1 |
| N00002 | 2 |
| N00003 | 2 |
| N00004 | 2 |
| N00005 | 1 |
| N00006 | 3 |

FIG. 14

Hdfs://localhost:9000/user/DataA.csv

Patient ID, Index_Patient_key, Hospitalization date, Discharge date, lab_test_A, Lab_test_B, Frequency of med_B, Frequency of med_C
N00001,N00001_0001,2012-01-01,2012-01-23,0.1,0.2,2.1,2.3
N00002,N00002_0001,2012-01-01,2012-01-23,0.1,0.2,2.1,2.3
N00003,N00003_0001,2012-01-01,2012-01-23,0.1,0.2,2.1,2.3
N00005,N00005_0001,2012-02-01,2012-02-14,0.9,0.3,2.4,2.5

FIG. 18

Hdfs://localhost:9000/user/DataB.csv

Patient ID, Index_Patient_key, Hospitalization date, Discharge date, lab_test_AA, Lab_test_BB, lab_test_CC, Frequency of med_BB, Frequency of med_CC
N00001,N00001_0001,2012-01-01,2012-01-23,0.1,0.2,2.1,2.3
N00003,N00003_0001,2012-01-01,2012-01-23,0.1,0.2,2.1,2.3
N00004,N00004_0001,2012-01-01,2012-01-23,0.1,0.2,2.1,2.3
N00005,N00005_0001,2012-02-01,2012-02-14,0.9,0.3,2.4,2.5

FIG. 19

Hdfs://localhost:9000/user/DataC.csv

Patient ID, Index_Patient_key, Hospitalization date, Discharge date, lab_test_AAA, Lab_test_BBB, Frequency of med_BBB, Frequency of med_CCC
N00001,N00001_0001,2012-01-01,2012-01-23,0.1,0.2,2.1,2.3
N00002,N00002_0001,2012-01-01,2012-01-23,0.1,0.2,2.1,2.3
N00004,N00004_0001,2012-01-01,2012-01-23,0.1,0.2,2.1,2.3
N00005,N00005_0001,2012-02-01,2012-02-14,0.9,0.3.2.4,2.5
N00006,N00006_0001,2012-01-01,2012-01-23,0.1,0.2,2.1,2.3

FIG. 20

DATA MANAGEMENT METHOD, APPARATUS AND SYSTEM FOR MACHINE LEARNING SYSTEM

BACKGROUND

Field

The present disclosure is directed to data management for machine learning (ML) systems, and more specifically, to handling machine learning systems for data having features that are protected by privacy and risk management systems.

Related Art

When creating ML systems, the problems that occur involve data selection and feature selection. In particular, several entities (e.g., hospitals, insurance companies, governments), store and manage data in proprietary formats and involve confidential information that forbids direct data access to outside vendors. Accordingly, if an ML system needs to utilize data from such entities, the engineers or data scientists working for the entity need to prepare their data based on their policy (e.g., access and privacy restrictions), ethics, knowledge, and vendor requests. Further, the selected data prepared by such engineers or data scientists working for the entity may be inappropriate as a training dataset due to missing data or bad data.

In related art implementations, the engineers and data scientists working for the entity, along with the data scientists trying to create an ML system thereby conduct trial and error to select features for the ML system due to the data access restrictions, which makes it difficult to create ML systems.

SUMMARY

Example implementations are directed to systems and methods for selecting appropriate data samples and features for an ML system. Although example implementations described herein involve patient data and hospitals for facilitating a healthcare decision support system, the example implementations described herein can be extended to other situations that involve severe data access restrictions, such as government entities, insurance companies, and so on.

As an example in the field of hospitals and healthcare providers, each hospital or healthcare provider utilizes a different data policy, and external vendors cannot access the data managed by the hospital or healthcare provider directly due to laws protecting patient data or electronic health records (EHR). In related art implementations, the hospital engineers/data scientists select data and give the vendor the privacy protected data through anonymization. The vendor only has partial access to data, as well as metadata access.

Example implementations described herein involve a "risk factor management component" that selects appropriate samples (e.g. patients) which have enough data sources regarding factors considered to be important based on the experienced risk factors at other entities, and is stored as metadata. The risk factor management puts more prioritization on some patients which have more data in the required data source than the other patients among all data sample candidates. In other words, the similarity of training data sample attributes can be criteria to select new sample sets.

In addition, the risk factor management selects valuable features effectively based on metadata derived from the experience of other entities.

The example implementations can thereby improve accuracy for ML systems as it utilizes daily system management in one entity repeatedly, and can also work for deploying the ML system into the other entities accordingly.

Aspects of the present disclosure involve a method to generate a trained model for first privacy protected data associated with a first facility, the method involving determining metadata of a second privacy protected data associated with a second facility, the metadata associated with features from the first privacy protected data associated with the first facility; determining, based on the metadata, a sample of the first privacy protected data associated with the first facility to be utilized in training the model; and training the model based on the sample of the first privacy protected data associated with the first facility.

Aspects of the present disclosure involve a computer program configured to generate a trained model for first privacy protected data associated with a first facility, the computer program having instructions involving determining metadata of a second privacy protected data associated with a second facility, the metadata associated with features from the first privacy protected data associated with the first facility; determining, based on the metadata, a sample of the first privacy protected data associated with the first facility to be utilized in training the model; and training the model based on the sample of the first privacy protected data associated with the first facility. The instructions of the computer program may be stored in a non-transitory computer readable medium configured to be executed by one or more processors.

Aspects of the present disclosure involve a system configured to generate a trained model for first privacy protected data associated with a first facility, the system having means for determining metadata of a second privacy protected data associated with a second facility, the metadata associated with features from the first privacy protected data associated with the first facility; means for determining, based on the metadata, a sample of the first privacy protected data associated with the first facility to be utilized in training the model; and means for training the model based on the sample of the first privacy protected data associated with the first facility.

Aspects of the present disclosure further involve an apparatus configured to generate a trained model for first privacy protected data associated with a first facility, the apparatus involving a processor, configured to determine metadata of a second privacy protected data associated with a second facility, the metadata associated with features from the first privacy protected data associated with the first facility; determine, based on the metadata, a sample of the first privacy protected data associated with the first facility to be utilized in training the model; and train the model based on the sample of the first privacy protected data associated with the first facility.

BRIEF DESCRIPTION OF DRAWINGS

FIG. 9 illustrates an example data model to manage model metadata, in accordance with an example implementation.

FIG. 10 illustrates an example of a table to describe prediction results, in accordance with an example implementation.

FIG. 11 illustrates an example table to show risk factors, in accordance with an example implementation.

FIG. 12 illustrates an example table to show importance cluster labels, in accordance with an example implementation.

FIG. 13 illustrates an example table to show feature vectors, in accordance with an example implementation.

FIG. 14 illustrates an example table to show patient priority labels, in accordance with an example implementation.

FIGS. 18 to 20 illustrate examples of datasources, in accordance with an example implementation.

DETAILED DESCRIPTION

Figure 1:
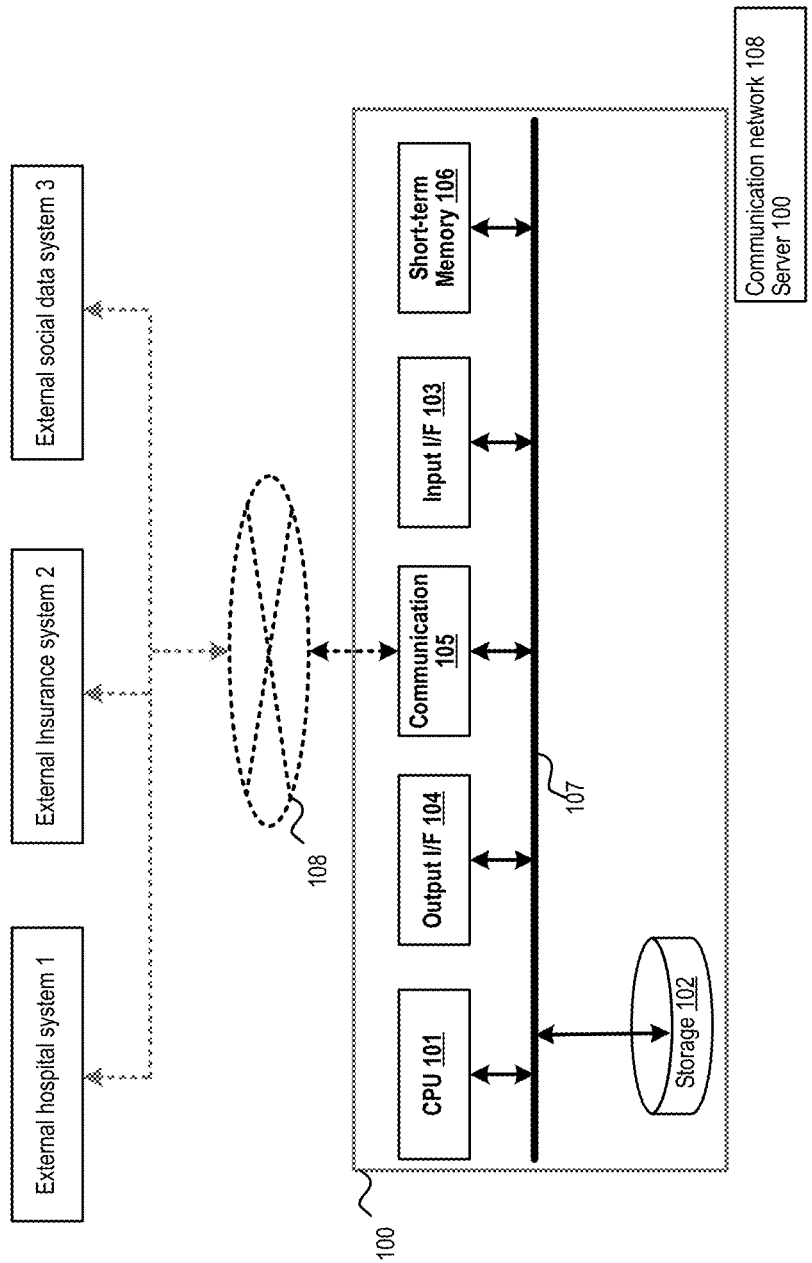
FIG. 1 illustrates an example of a hardware configuration, in accordance with an example implementation.

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or administrator control over certain aspects of the implementation, depending on the desired implementation of one of ordinary skill in the art practicing implementations of the present application. Selection can be conducted by a user through a user interface or other input means, or can be implemented through a desired algorithm. Example implementations as described herein can be utilized either singularly or in combination and the functionality of the example implementations can be implemented through any means according to the desired implementations.

Example implementations described herein are directed to selecting appropriate data samples and features for training ML models that conduct prediction analysis based on risk factors, in a system that facilitates the use of privacy protected data, such as a healthcare decision support system. In example implementations described herein, a risk factor management component selects appropriate samples (e.g. patients, persons with private data) which have enough data sources for use in the ML model, thereby bringing highly important factors based on the experienced risk factors (e.g., risk factors at other hospitals such as Hospital A), which is stored as metadata. The risk factor management puts more prioritization on some patients or persons which have more data in the required data source than the other patients or persons among all data sample candidates. In other words, the attribute similarity of the training data sample would be criteria to select a new sample sets. In addition, the risk factor management selects valuable features effectively based on metadata derived from experiences of other facilities such as hospitals.

Such example implementations can improve the ML accuracy as the processes described herein can facilitate daily system management in a facility such as a hospital, and the ML system can be extended for deployment in other facilities (e.g., other hospitals) without exposing privacy protected data from the underlying facility.

Collected data can vary widely in size and type of data stored within a connected system such as a healthcare system, each patient can be at different data collection level. For example, some doctors are likely to retain their notes for their patients, but some others do not retain such notes as there are no specific standards or requirements for doctors. Such doctor notes are sometimes useful for recognizing and predicting the future condition of the patient. Therefore, a training model that involves doctor notes needs to be more sophisticated in parsing through the differences. Further, private patient health data can also vary widely, and can involve data such as data from a smart phone health application. Such unconventional data may also be included for a private training model.

FIG. 1 illustrates an example of a hardware configuration, in accordance with an example implementation. Server 100 involves elements to facilitate the model management system, which can include central processing unit (CPU) 101, storage 102 input 103, and output 104 interface (I/F), communication network I/F 105 and short-term memory 106. Those are connected with each other through a bus 107. The server 100 is connected to external entities such as hospital systems through network 108, which can be in the form of a local area network (LAN) or wide area network (WAN) to send data or receive in a bidirectional or one directional way. CPU 101 can be in the form of a physical hardware processor, or as a combination of hardware and software processors in accordance with the desired implementation.

As will be described in example implementations herein, the server 100 is an apparatus configured to generate a trained model for first privacy protected data associated with a first facility. In such an example implementation, CPU 101 can be configured to determine metadata of a second privacy protected data associated with a second facility, the metadata associated with features from the first privacy protected data associated with the first facility; determine, based on the metadata, a sample of the first privacy protected data associated with the first facility to be utilized in training the model; and train the model based on the sample of the first privacy protected data associated with the first facility as illustrated in FIGS. 2-7.

In example implementations, the metadata is indicative of a relationship between the features, types of data sources associated with the features, and the model to be trained as illustrated in FIG. 9.

Depending on the desired implementation, the features are based on risk factors, wherein the features are selected by the CPU 101 based on an importance associated with the risk factors, and wherein the training the model is further based on the selected features as illustrated in FIGS. 3, 6-8 and 11.

Figure 4:
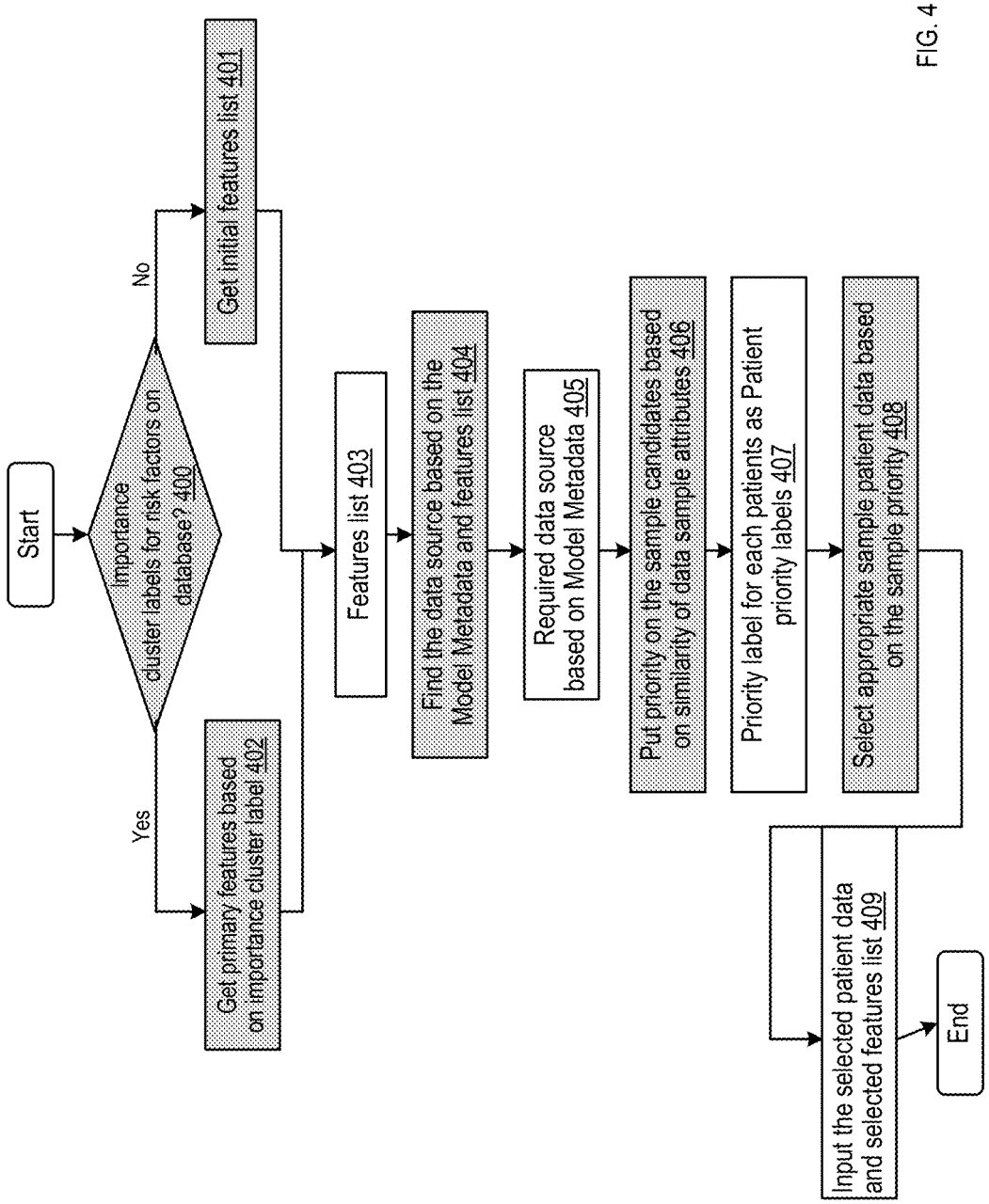
FIG. 4 illustrates the detailed flow of the risk factor management component, in accordance with an example implementation.

In example implementations, the CPU 101 is configured to determine the sample of the first privacy protected data associated with the first facility based on a volume of the first privacy protected data as illustrated in FIG. 4.

In example implementations, the model is trained to output risk factors, importance values for each of the risk factors, and a readmission risk score as illustrated in FIG. 10.

Figure 15:
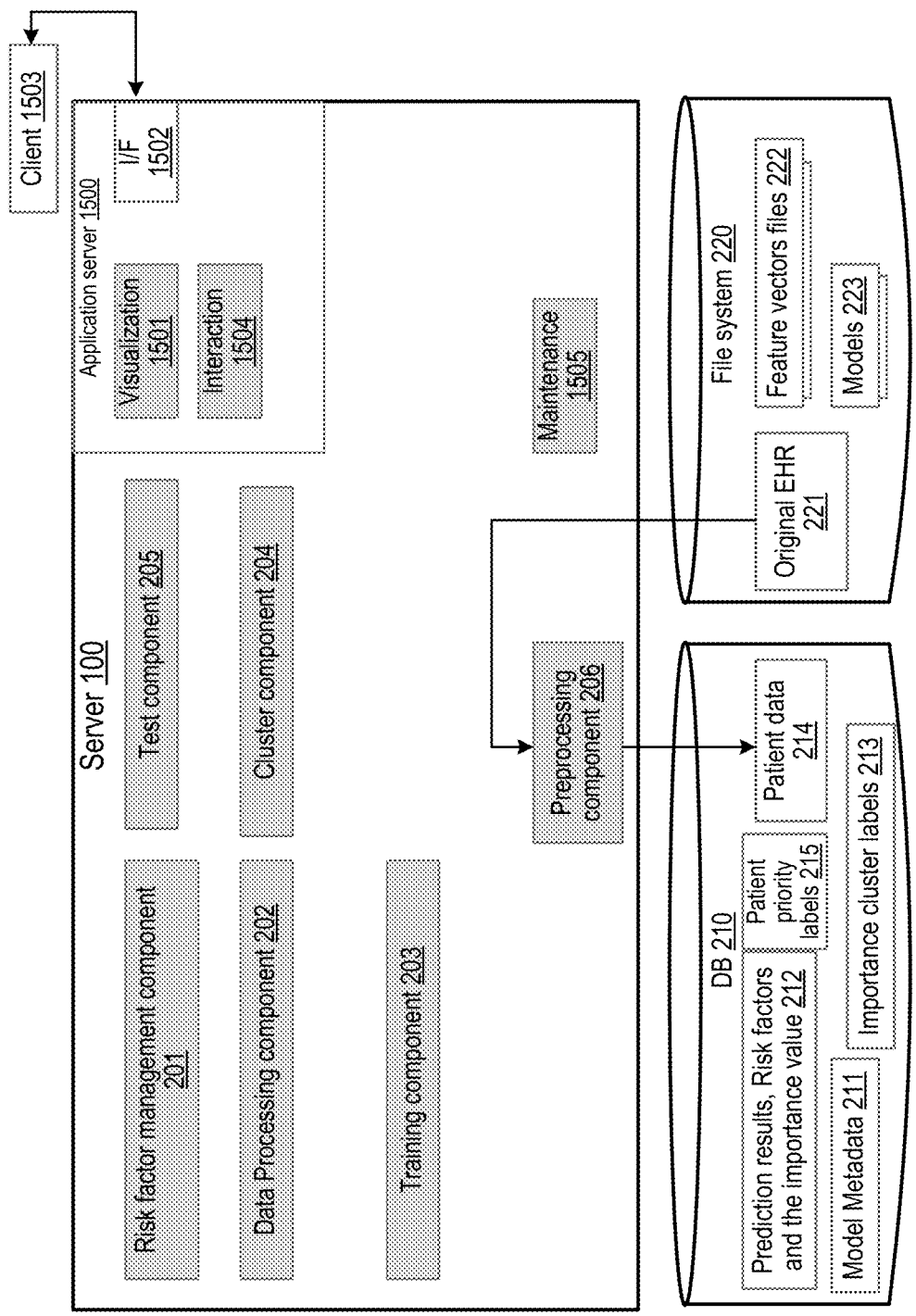
FIG. 15 illustrates another example of the system, in accordance with an example implementation.
Figure 16:
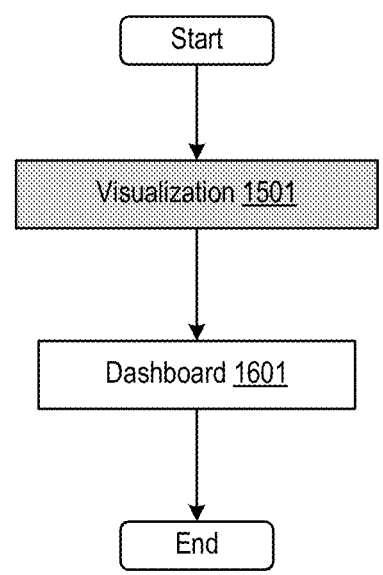
FIG. 16 illustrates an example of the visualization main flow diagram, in accordance with an example implementation.
Figure 17:
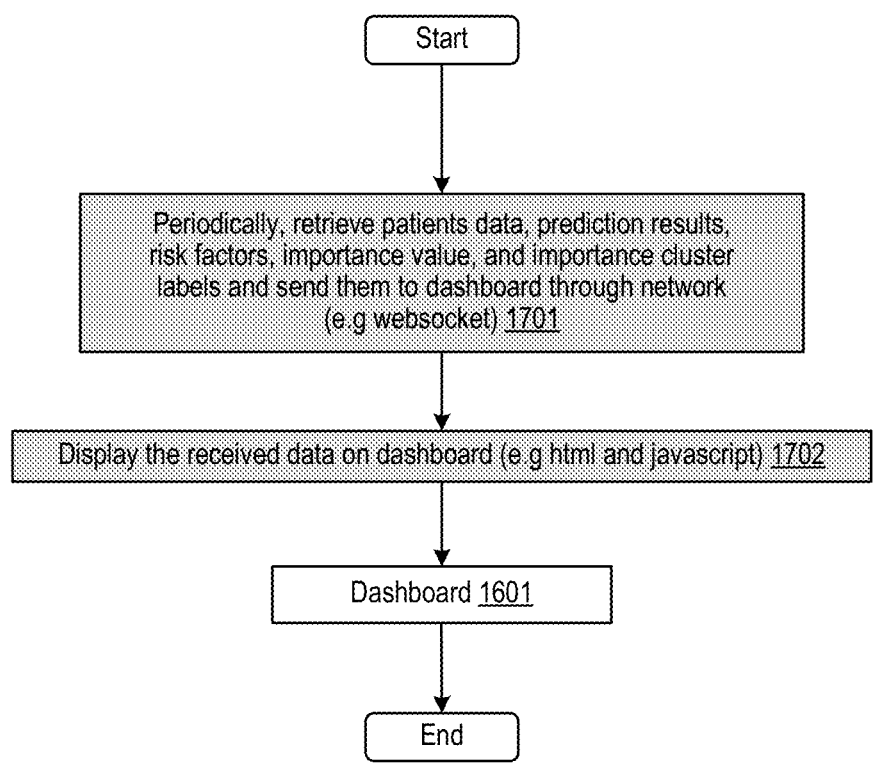
FIG. 17 illustrates a visualization detailed flow diagram, in accordance with an example implementation.

In example implementations, the CPU 101 is further configured to execute the trained model against the first privacy protected data periodically, and generate a visualization comprising the output of the trained model, the visualization being updated periodically as illustrated in FIGS. 15-17.

Figure 2:
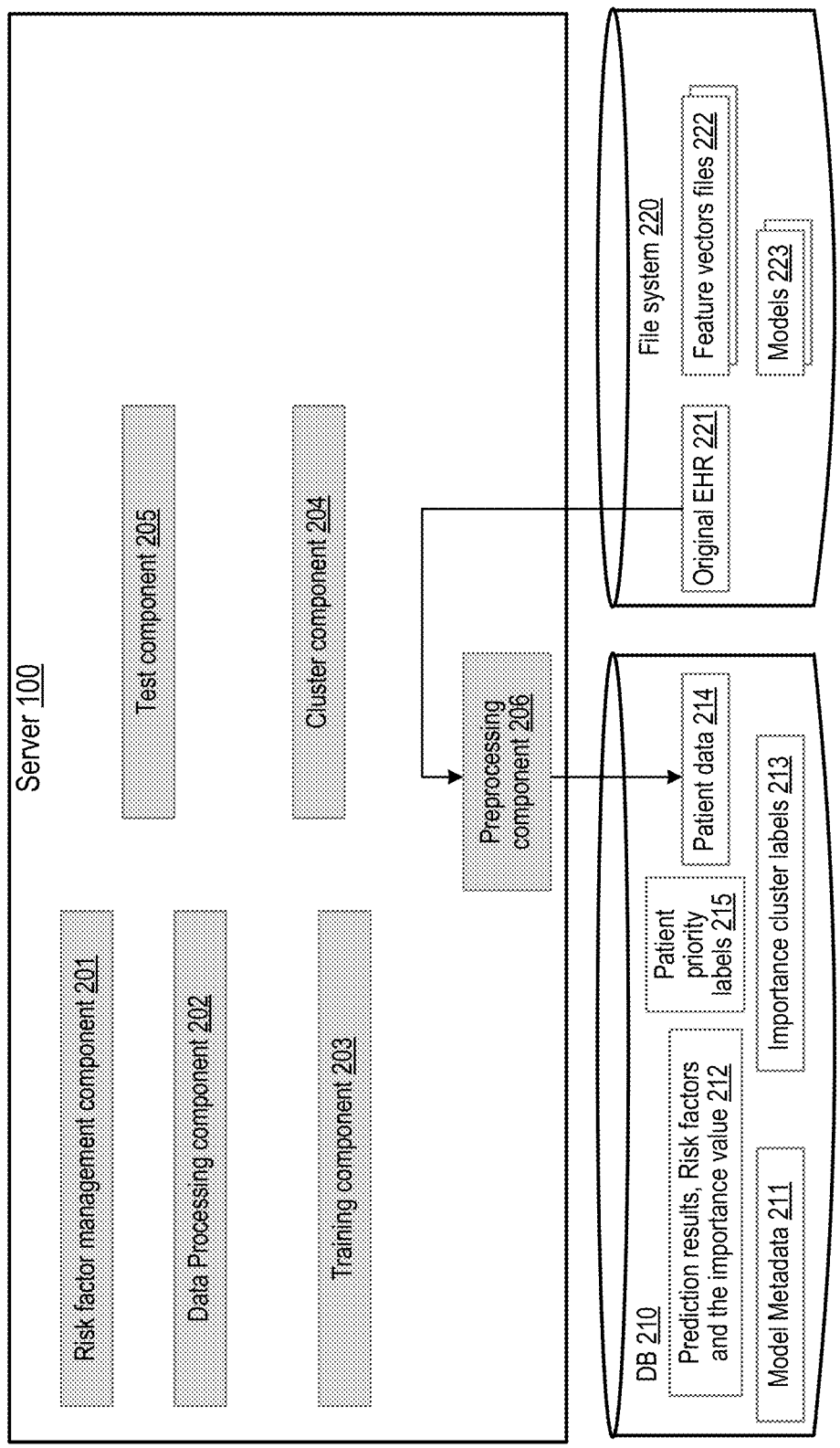
FIG. 2 illustrates system components to select appropriate data samples and features, in accordance with an example implementation.

FIG. 2 illustrates system components to select appropriate data samples and features, in accordance with an example implementation. There can be components such as risk factor management component 201, data processing component 202, training component 203, cluster component 204, test component 205 and preprocessing component 206. In the storage 102, there can be a database (DB) 210 and file system and 220 facilitated by the storage. DB 210 can store model metadata 211, prediction results/risk factors/importance values 212, importance cluster labels 213, patient data 214, and patient priority labels 215. File system 220 can involve anonymized EHR data 221 derived from hospitals, feature vectors files 222, and machine-learning models 223.

In an example implementation, server 100 is configured to generate a trained model for first privacy protected data associated with a first facility, and can be located at the first facility with access to the original EHR 221 through a preprocessing component 206. DB 210 may also include information from another server associated with second privacy protected data associated with a second similar type of facility (e.g., another hospital, another insurance company, etc.) with the same architecture that provides model metadata 211, and prediction results, risk factors and importance values 212. As illustrated in FIGS. 9-12, such model metadata 211 can indicate what features are utilized to generate various types of models, and can thus be associated with the same features extracted from the first privacy protected data (e.g., Original EHR 221 of the first facility). In such an example implementation, a sample of the first privacy protected data associated with the first facility can be determined for use in training the model based on the features indicated in the model metadata 211 as obtained from the second facility through the process described in FIG. 4.

Through such an example implementation, the manager of the server 100 at the first facility does not have to determine which of the patient data to request in generating the ML model as the features can be derived based on the model metadata 211 of the second facility and samples can be obtained accordingly. Further, because the metadata associated with the privacy protected data of the second facility does not contain any privacy information, the second privacy protected data can thereby be isolated from the first facility, thereby avoiding contamination of privacy protected data between facilities while allowing the first facility to incorporate results of model training from the second facility to conduct its own machine learning model training. Similarly, the model metadata 211 and prediction results, risk factors and importance values 212 generated from the example implementations as utilized in the first facility can thereby be provided to other facilities that also generate machine learning models without exposing the other facilities to the privacy protected data in the EHR system. In addition, because the model metadata is used to determine the samples to be utilized, the resulting machine learning model trained by the example implementations have higher accuracy than related art systems as appropriate samples can be directly targeted to the EHR system.

Figure 3:
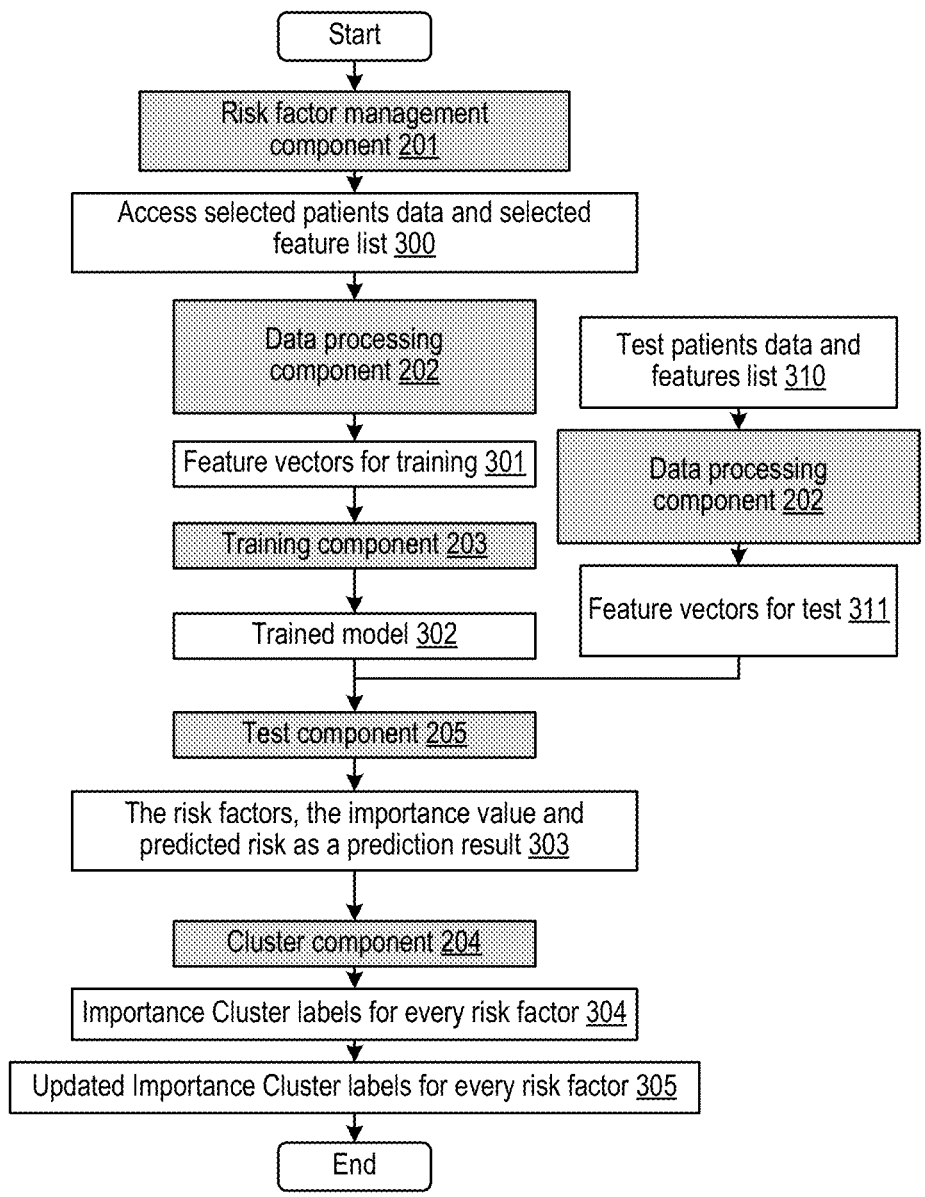
FIG. 3 illustrates an example flow diagram for the system of FIG. 2, in accordance with an example implementation.

FIG. 3 illustrates an example flow diagram for the system of FIG. 2, in accordance with an example implementation. This main flow illustrates a process for making a machine learning model and using the model for prediction. Therefore, the process runs periodically (e.g., monthly) in an automatic manner or manually by users in accordance with the desired implementation. The risk factor management component 201 accesses the database as will be described in FIG. 4, and selects an appropriate sample/patient data (e.g., EHR data) and a selected feature list that indicates the types of features on a list. Then, data processing component receives the selected patient data and selected feature list, and utilizes such information to generate feature vectors for training 301. During this process, the data processing component 202 may also makes feature vectors for test data 311 from the test patient data and features list 310.

Then, training component 203 takes the feature vectors and generates a trained model 302 through any ML training process in accordance with the desired implementation. Test component 205 conducts a ML test by using the trained model and feature vectors for test samples. Test component 205 outputs the risk factors, the importance values, and predicted risk as a prediction result 303. After running certain tests, the cluster component 204 put labels on the risk factors based on the multiples test results at 304. The label indicates the relative importance of each of the risk factors for the prediction result. For each predetermined time interval, or every number of tests, the system can be configured to update the importance cluster labels for every risk factor on the DB at 305.

FIG. 4 illustrates the detailed flow of the risk factor management component 201, in accordance with an example implementation. At 400, the risk factor management component 201 tries to access importance cluster labels by checking if there are such cluster labels available on the DB. If there is no importance cluster label yet on the database (No), the system gets the initial features list 401, otherwise (Yes) the system obtains the primary features based on the importance cluster label such as higher importance labels over certain criteria (e.g. top 40 or over the average) at 402.

The types of features obtained at 401 or 402 are then placed in the features list 403. The system finds the data source by retrieving the data source from the model metadata 405 when it receives the features list at 404. After finding out which data source is required at 405, the system puts priority on the sample candidates (e.g. patients) based on some priority criteria, e.g., the volume of data associated with each sample at 406. For example, some patients have general lab records, medical records, and hospital records whereas some other patients may only have general lab and medical records, or may include social history data additionally. The priority is output as patient priority labels at 407. Then, the system selects the appropriate sample patient data based on the priority at 408. If there are enough highest priority samples (e.g., the number of the highest priority patients meets the required number of training data), the samples with the highest priority are selected. If there are not enough samples with the highest priority labels, the next priority level samples are selected. This selection process is repeatedly conducted from the highest priority to the lowest priority until the required amount of training data is selected. Then, the selected patient data and feature list is provided at 409.

FIGS. 18, to 20 illustrate examples of datasources to provide some features, in accordance with an example implementation. FIG. 18 is an example datasource file named DataA.csv, FIG. 19 is an example datasource file named DataB.csv, and FIG. 20 is an example datasource file named DataC.csv. Each file has a header on the first row, which describes the column name for the data from the second row. In these three example files, Patient ID N00001 and N00005 are included in all the files, which brings that those patients are the most prioritized.

Figure 21:
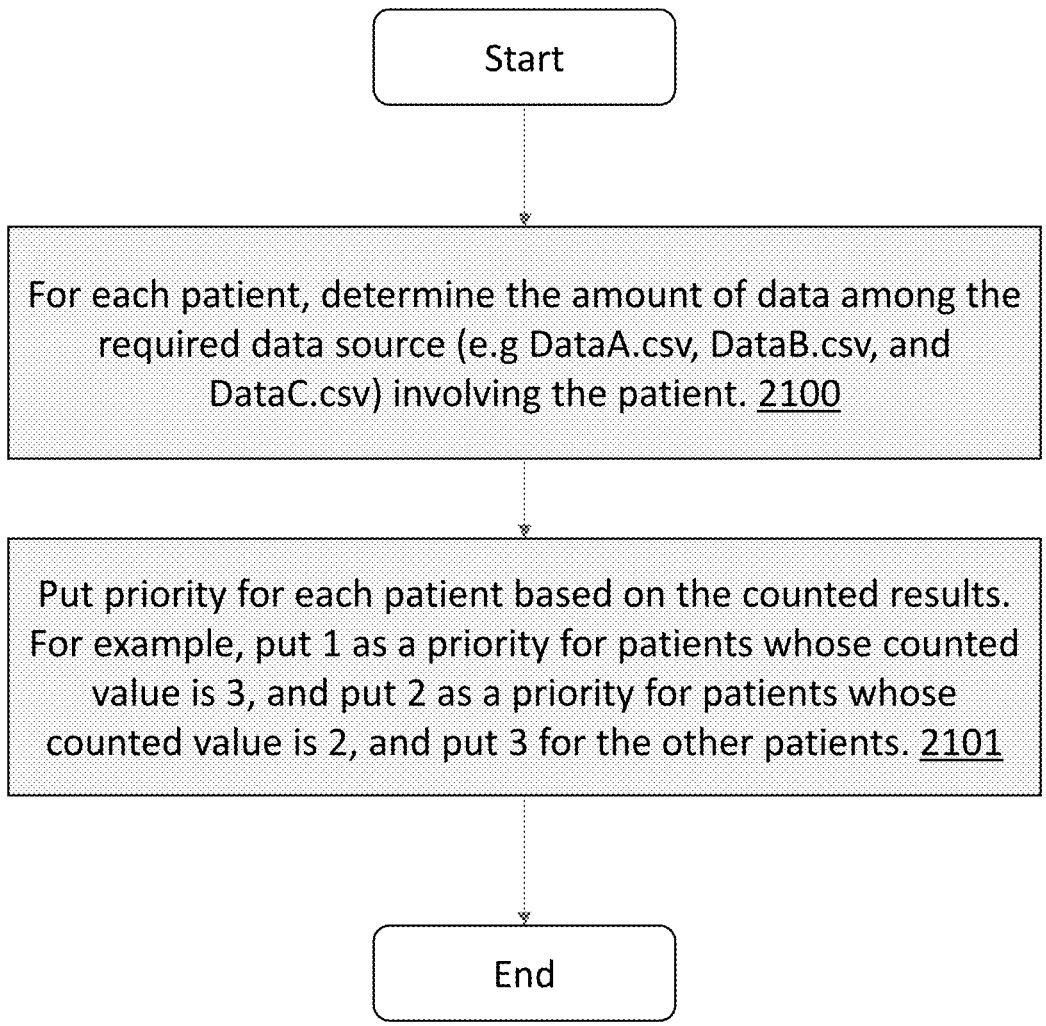
FIG. 21 illustrates an example of a priority calculation process in accordance with an example implementation.

FIG. 21 illustrates an example flow diagram to output the patient priority based on data sample attribute's similarity at 406. For example, when priority is calculated based on the amount of data involving each patient among the required data sources in an implementation, the system counts the number of data sources for each patient at 2100. Then, the system classifies all the counted values into 3 priority levels such as 1, 2, 3 in order from the largest number of the counted value at 2101.

Figure 5:
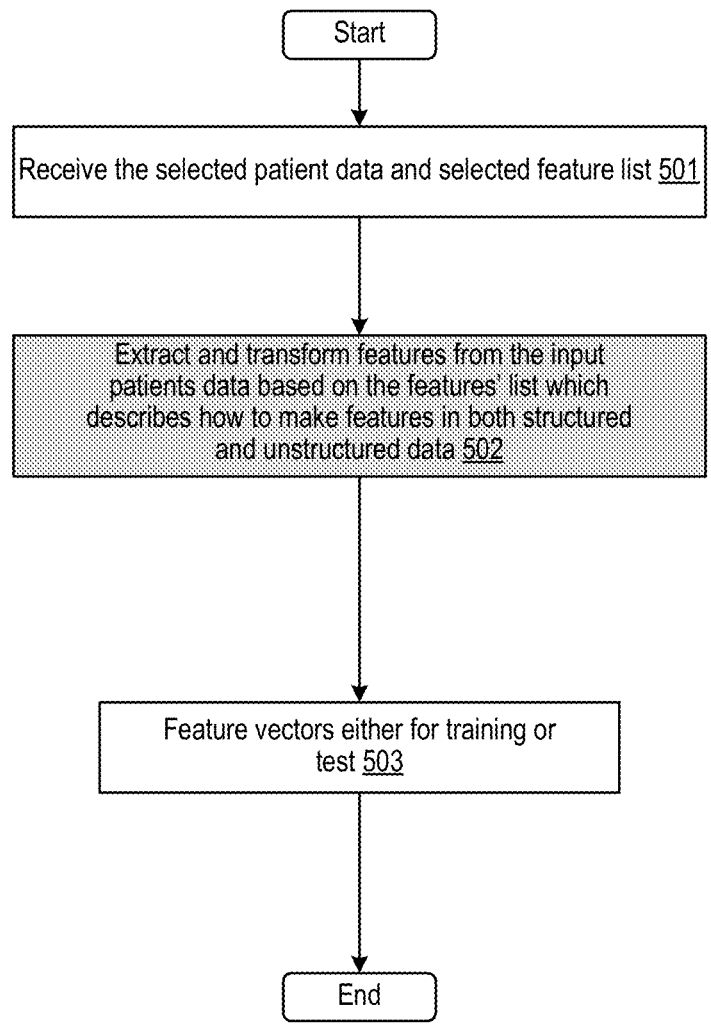
FIG. 5 illustrates the flow diagram for the data processing component to make feature vectors, in accordance with an example implementation.

FIG. 5 illustrates the flow diagram for the data processing component 202 to make feature vectors, in accordance with an example implementation. The component 202 receives the selected patient data and selected feature list at 501, and extracts and transforms features from the input patient data based on the input list of features at 502. Then, the component outputs the features vector for training or test (e.g., feature_vector.h5) at 503.

Figure 6:
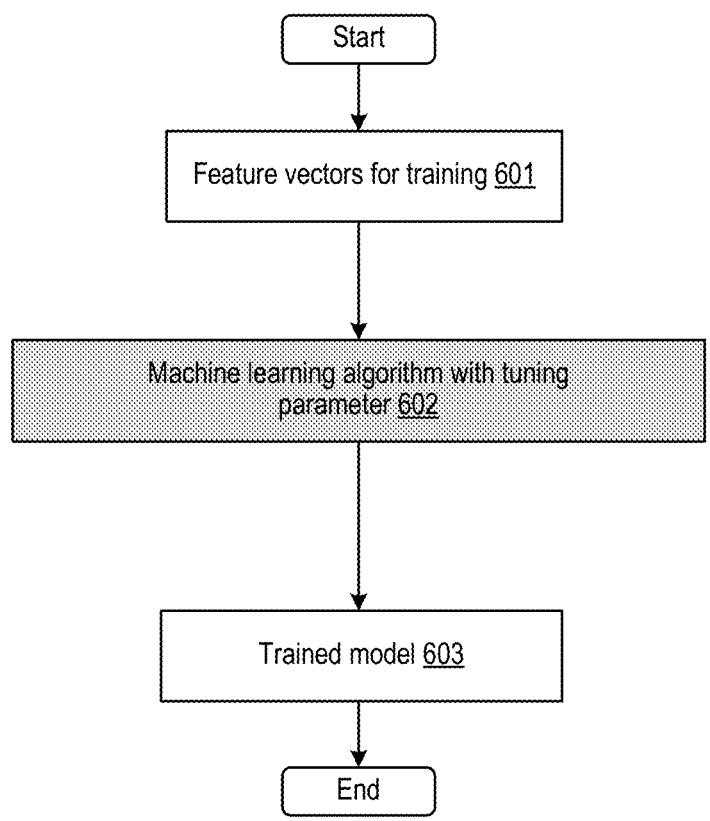
FIG. 6 illustrates an example flow diagram for the training component, in accordance with an example implementation.

FIG. 6 illustrates an example flow diagram for the training component 203, in accordance with an example implementation. This component 203 receives features vectors for training at 601 and trains the feature vectors by using a machine learning algorithm 602 (e.g. linear regression, neural network or deep learning) to produce a trained model 603 which is configured to output risk factors eventually as a prediction results.

Figure 7:
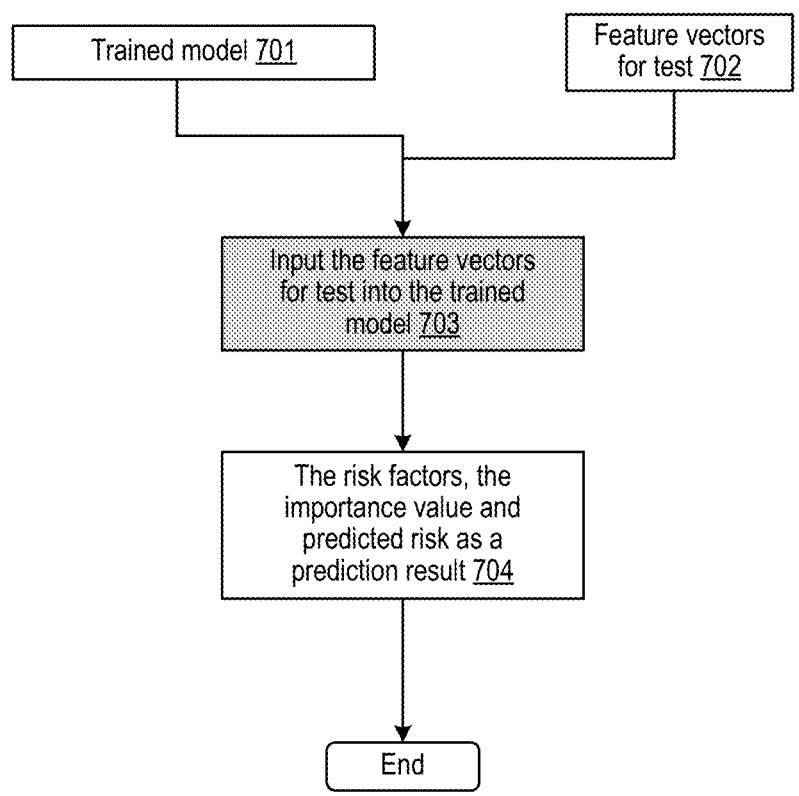
FIG. 7 illustrates an example flow diagram for the test component, in accordance with an example implementation.

FIG. 7 illustrates an example flow diagram for the test component 205, in accordance with an example implementation. This component 205 receives a trained model 701 and feature vectors for test 702, and inputs the feature vectors into the trained model and executes a test at 703 to output the predicted risk, risk factors and the importance values as a prediction result at 704.

Figure 8:
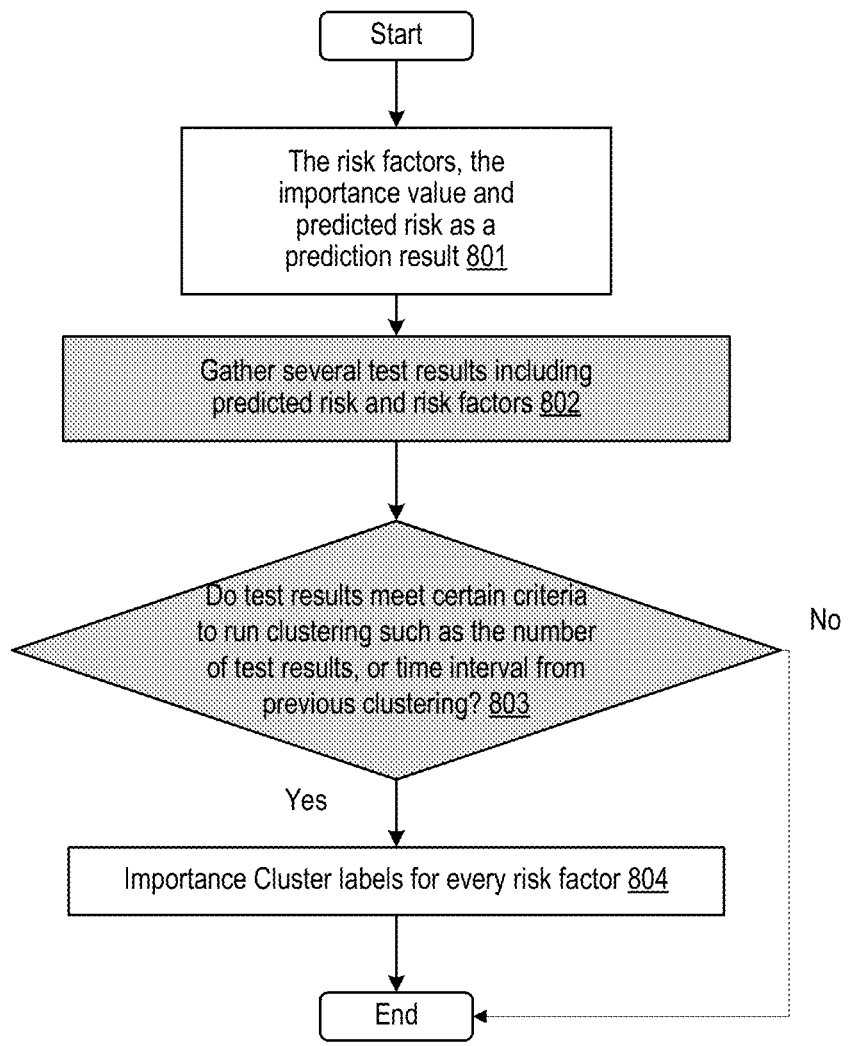
FIG. 8 illustrates an example flow diagram for the cluster component, in accordance with an example implementation.

FIG. 8 illustrates an example flow diagram for the cluster component 204, in accordance with an example implementation. The component receives prediction results at 801 and collects multiple test results which can include the predicted risk probability, the risk factors and the importance values at 802. Then at 803, if the situation meets certain criteria to run clustering (Yes), such as the number of test results meeting a certain criteria or a predetermined period of time after the last clustering has lapsed, the component 204 starts clustering (e.g. K-means) by using the risk factors and the importance values. Then, the importance cluster labels for every risk factor are output at 804. Otherwise (No), the process can end or can be looped back to 803 to wait until the conditions are met, depending on the desired implementation.

FIG. 9 illustrates an example data model to manage model metadata, in accordance with an example implementation. The FEATURESMETA, FEATURESELEMENT, DATASOURCEELEMENT, MODELMETA and TESTMETA store various metadata that reference machine learning models, features and the test results (e.g., types of features), how to make the features as RECIPE, types of data sources, model parameters and test results, in accordance with the desired implementation. As shown in FIG. 9, the model metadata is indicative of a relationship between the features, types of data sources associated with the features, and the model to be trained. For example, in MODELMETA, the identifier for the model to be trained is designated as MODEL_ID, which utilize the set of features designated by FEATURES_ID, wherein the model to be trained is trained according to the algorithm and tuning parameters specified in the metadata ALGORITHM, and TUNING PARAM respectively. FEATURES_ID can then be utilized to determine the DATASOURCE_ID to determine what volume of data is required from what types of sources to effectively train the model.

FIG. 10 illustrates an example of a table to describe prediction results, in accordance with an example implementation. This table has row identifier (ID) as prediction_result_id, model ID as Model_ID, sets of features ID as FEATURES_ID, test patient result ID as Test Patient_ID and readmission prediction risk as Readmission_Prediction_result. As described herein, the model is trained to produce the prediction results as illustrated in FIG. 10, with the sets of features indicative of the risk factors and the readmission prediction risk indicative of a readmission risk score. The readmission risk score can be implemented according to any desired implementation to reflect the probability of a revisit to the facility by the test patient indicated in Test Patient D given the prediction result and the set of risk factors. As will be shown in FIG. 11, each of the features can also be associated with an importance value, which can also be output for visualization using the systems of FIGS. 15-17.

FIG. 11 illustrates an example table to show risk factors, in accordance with an example implementation. This table has prediction result ID as Prediction_result_ID, feature element ID as Feature_element_id and importance value for each feature as Importance_value. As shown in FIG. 11, for a desired type of prediction, the model can be trained based on the associated importance value of the risk factors associated with the features. As described herein, in an example implementation involving hospitals, the features can be utilized as risk factors for conducting prediction of a condition, with the importance value indicative of how important such a risk factor is in predicting such a condition. The importance value can be derived according to any desired implementation.

FIG. 12 illustrates an example table to show importance cluster labels, in accordance with an example implementation. This has the ID of sets of features as Features_id, feature element ID as Features_element_id, and importance cluster label as Label.

FIG. 13 illustrates an example table to show feature vectors, in accordance with an example implementation. This table has patient ID as Patient_ID, index of hospitalization ID for each patient as Index_Patient_key, results for lab test A result as Lab_test_A, and frequency of medicine B as Frequency of med_B, and so on, as features, in accordance with the desired implementation.

FIG. 14 illustrates an example table to show patient priority labels, in accordance with an example implementation. This table has Patient_ID and data selection priority to show the priority to be selected as a training data. For example, N00001 and N00005 are the most prioritized data sample as a training data while N00002, N00003, N00004 are the second prioritized data sample, and N00001 and N00006 are the least prioritized data samples.

FIG. 15 illustrates another example of the system, in accordance with an example implementation. The difference is the addition of a visualization component 1501 and an interaction component 1504 in an application server 1500 which a client 1503 accesses through the interface 1502 by using protocols such as Hypertext Transfer Protocol (HTTP) and maintenance component 1505. The application server 1500 can have the same configuration as that of the server 100 illustrated in FIG. 1. In example implementations, when the trained model as described herein is executed, such execution can be conducted on the data periodically as illustrated in FIG. 17, and the visualization can be updated accordingly (e.g., periodically) in accordance with the desired implementation.

FIG. 16 illustrates an example of the visualization main flow diagram, in accordance with an example implementation. The visualization procedure is executed by visualization component 1501, as illustrated in FIG. 17. At 1601, the flow provides the results of the visualization on a dashboard, which is configured to display results to the client device 1503.

FIG. 17 illustrates a visualization detailed flow diagram, in accordance with an example implementation. Specifically, this component 1501 periodically retrieves patent data, prediction results, risk factors, importance values and importance cluster labels from the database, transforms the format, and sends the data to the dashboard 1601 through a network (e.g. websocket) at 1701. Then, the data is displayed on a dashboard 1601, which can utilize HTML, Javascript, or other methods in accordance with the desired implementation.

Figure 22:
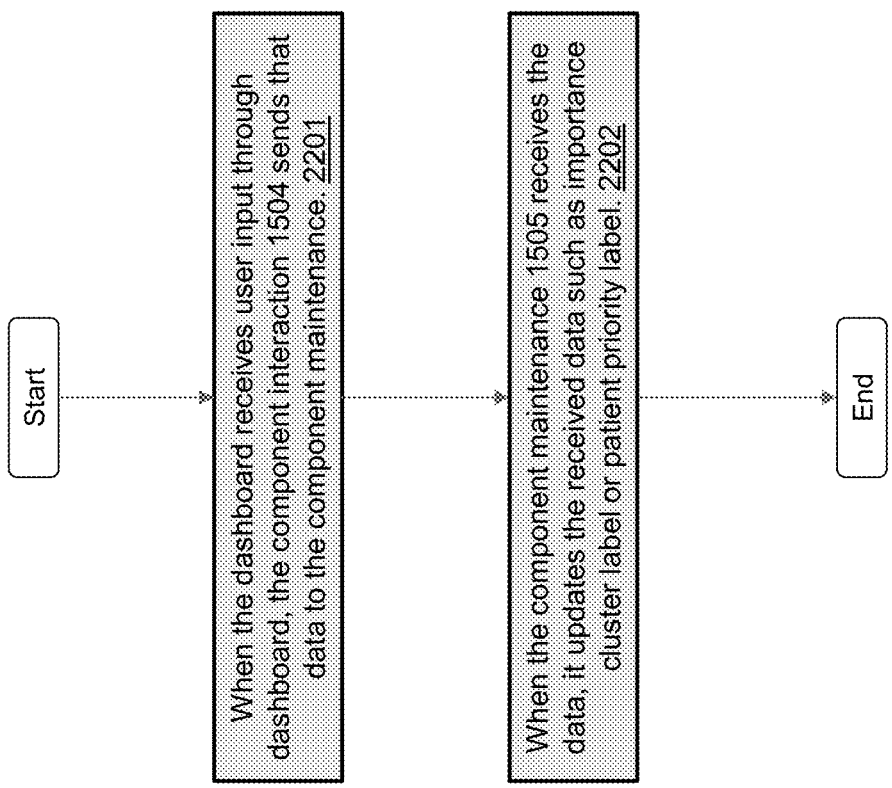
FIG. 22 illustrates a flow diagram for user interaction, in accordance with an example implementation.

FIG. 22 illustrates a flow diagram for user interaction, in accordance with an example implementation. When the component 1503 receives user inputs from this system to update stored data such as importance cluster labels or patient priority labels, the input data is sent to the application server at 1500 through the interface at 1502. The component interaction at 1504 sends the received data to the component maintenance 1505 at 2201. Then, the component maintenance 1505 updates the stored data on DB at 210 by using the received data at 2202. Such updates to the stored data can include updates to the importance cluster labels at 213 or patient priority labels at 215.

Figure 23:
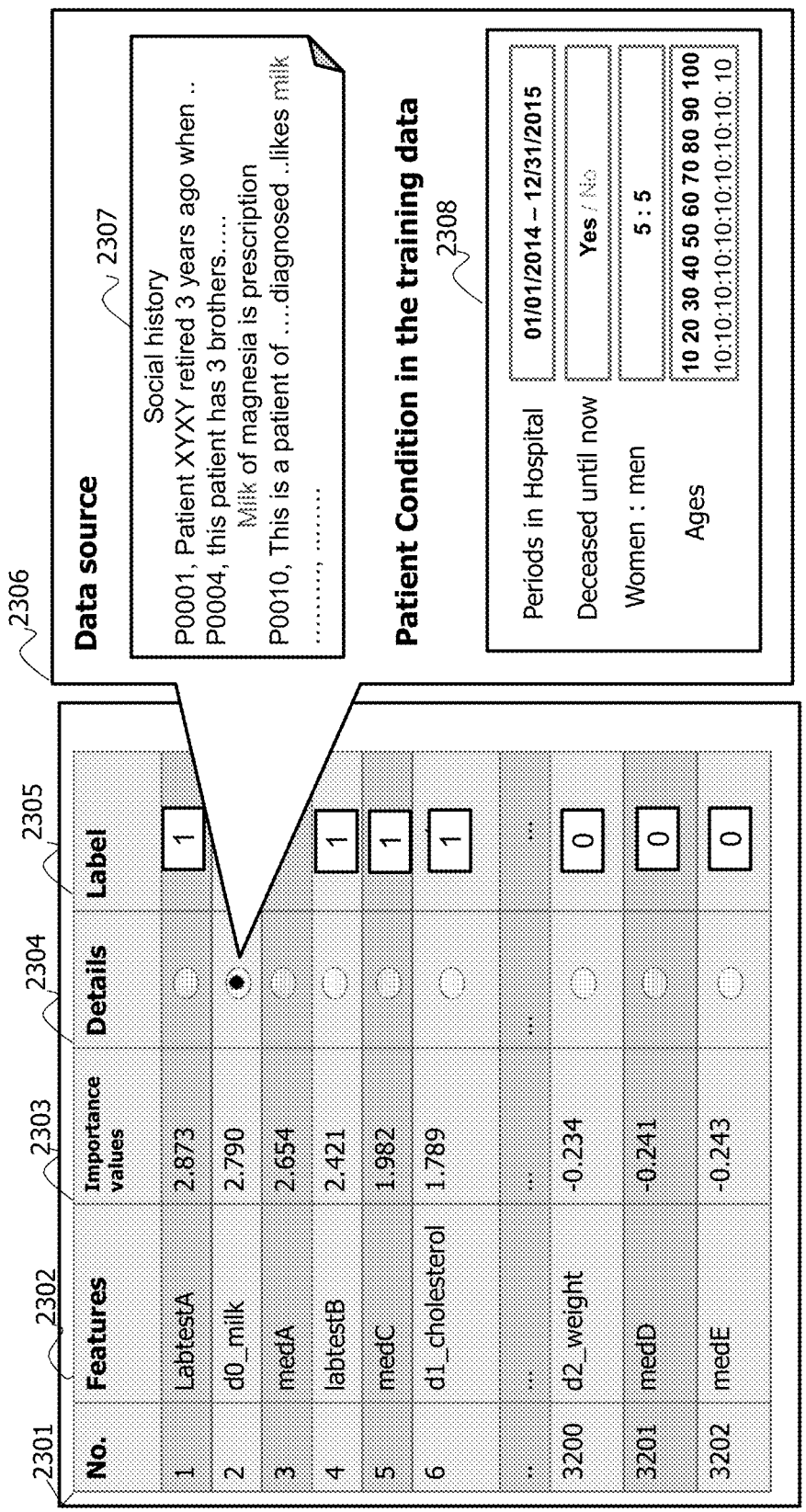
FIG. 23 illustrates an example dashboard of a client device, in accordance with an example implementation.

FIG. 23 illustrates an example dashboard of the client device 1503, in accordance with an example implementation. The dashboard can provide information such as the rank of importance values at 2301 of the features 2302, the importance values of the features at 2303, the check box column Details to provide an interface to open the detailed information at 2304, and the input column as label to select the features as the importance cluster label at 2305 in the main display. For example, Label has 1 at first, a user input different values as Label (e.g. 0 or 1) on 2305. When a user selects one feature by clicking details on 2304, the system opens interface 2306. This interface 2306 displays the data source of the feature at 2307 and data condition (e.g. patient condition in the training data) at 2308.

Some portions of the detailed description are presented in terms of algorithms and symbolic representations of operations within a computer. These algorithmic descriptions and symbolic representations are the means used by those skilled in the data processing arts to convey the essence of their innovations to others skilled in the art. An algorithm is a series of defined steps leading to a desired end state or result. In example implementations, the steps carried out require physical manipulations of tangible quantities for achieving a tangible result.

Unless specifically stated otherwise, as apparent from the discussion, it is appreciated that throughout the description, discussions utilizing terms such as "processing," "computing," "calculating," "determining," "displaying," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

Example implementations may also relate to an apparatus for performing the operations herein. This apparatus may be specially constructed for the required purposes, or it may include one or more general-purpose computers selectively activated or reconfigured by one or more computer programs. Such computer programs may be stored in a computer readable medium, such as a computer-readable storage medium or a computer-readable signal medium. A computer-readable storage medium may involve tangible mediums such as, but not limited to optical disks, magnetic disks, read-only memories, random access memories, solid state devices and drives, or any other types of tangible or non-transitory media suitable for storing electronic information. A computer readable signal medium may include mediums such as carrier waves. The algorithms and displays presented herein are not inherently related to any particular computer or other apparatus. Computer programs can involve pure software implementations that involve instructions that perform the operations of the desired implementation.

Various general-purpose systems may be used with programs and modules in accordance with the examples herein, or it may prove convenient to construct a more specialized apparatus to perform desired method steps. In addition, the example implementations are not described with reference to any particular programming language. It will be appreciated that a variety of programming languages may be used to implement the teachings of the example implementations as described herein. The instructions of the programming language(s) may be executed by one or more processing devices, e.g., central processing units (CPUs), processors, or controllers.

As is known in the art, the operations described above can be performed by hardware, software, or some combination of software and hardware. Various aspects of the example implementations may be implemented using circuits and logic devices (hardware), while other aspects may be implemented using instructions stored on a machine-readable medium (software), which if executed by a processor, would cause the processor to perform a method to carry out implementations of the present application. Further, some example implementations of the present application may be performed solely in hardware, whereas other example implementations may be performed solely in software. Moreover, the various functions described can be performed in a single unit, or can be spread across a number of components in any number of ways. When performed by software, the methods may be executed by a processor, such as a general purpose computer, based on instructions stored on a computer-readable medium. If desired, the instructions can be stored on the medium in a compressed and/or encrypted format.

Moreover, other implementations of the present application will be apparent to those skilled in the art from consideration of the specification and practice of the teachings of the present application. Various aspects and/or components of the described example implementations may be used singly or in any combination. It is intended that the specification and example implementations be considered as examples only, with the true scope and spirit of the present application being indicated by the following claims.

What is claimed is:

1. A method to generate a trained model for first privacy protected data associated with a first facility, the method comprising:
determining metadata derived from second privacy protected data associated with a second facility, the metadata associated with features from the first privacy protected data associated with the first facility, the metadata indicative of a relationship between the features, types of data sources associated with the features, and the model to be trained as utilized in training one or more model at the second facility;
determining, based on the features and the relationship between the features, types of data sources associated with the features, and the model to be trained, a sample of the first privacy protected data associated with the first facility to be utilized in training the model at the first facility; and
training the model based on the sample of the first privacy protected data associated with the first facility.

2. The method of claim 1, wherein the features are based on risk factors, wherein the features are selected based on an importance associated with the risk factors, and wherein the training the model is further based on the selected features.

3. The method of claim 1, wherein the determining the sample of the first privacy protected data associated with the first facility is based on a volume of the first privacy protected data.

4. The method of claim 1, wherein the model is trained to output risk factors, importance values for each of the risk factors, and a readmission risk score.

5. The method of claim 1, further comprising executing the trained model against the first privacy protected data periodically, and generating a visualization comprising the output of the trained model, the visualization being updated periodically.

6. A non-transitory computer readable medium, storing instructions to generate a trained model for first privacy protected data associated with a first facility, the instructions comprising:
determining metadata derived from second privacy protected data associated with a second facility, the metadata associated with features from the first privacy protected data associated with the first facility, the metadata indicative of a relationship between the features, types of data sources associated with the features, and the model to be trained as utilized in training one or more model at the second facility;
determining, based on the features and the relationship between the features, types of data sources associated with the features, and the model to be trained, a sample of the first privacy protected data associated with the first facility to be utilized in training the model at the first facility; and
training the model based on the sample of the first privacy protected data associated with the first facility.

7. The non-transitory computer readable medium of claim 6, wherein the features are based on risk factors, wherein the features are selected based on an importance associated with the risk factors, and wherein the training the model is further based on the selected features.

8. The non-transitory computer readable medium of claim 6, wherein the determining the sample of the first privacy protected data associated with the first facility is based on a volume of the first privacy protected data.

9. The non-transitory computer readable medium of claim 6, wherein the model is trained to output risk factors, importance values for each of the risk factors, and a readmission risk score.

10. The non-transitory computer readable medium of claim 6, the instructions further comprising executing the trained model against the first privacy protected data periodically, and generating a visualization comprising the output of the trained model, the visualization being updated periodically.

11. An apparatus configured to generate a trained model for first privacy protected data associated with a first facility, the apparatus comprising:
a processor, configured to:
determine metadata derived from second privacy protected data associated with a second facility, the metadata associated with features from the first privacy protected data associated with the first facility, the metadata indicative of a relationship between the features, types of data sources associated with the features, and the model to be trained as utilized in training one or more model at the second facility;
determine, based on the features and the relationship between the features, types of data sources associated with the features, and the model to be trained, a sample of the first privacy protected data associated with the first facility to be utilized in training the model at the first facility; and
train the model based on the sample of the first privacy protected data associated with the first facility.

12. The apparatus of claim 11, wherein the features are based on risk factors, wherein the features are selected based on an importance associated with the risk factors, and wherein the training the model is further based on the selected features.

13. The apparatus of claim 11, wherein the processor is configured to determine the sample of the first privacy protected data associated with the first facility based on a volume of the first privacy protected data.

14. The apparatus of claim 11, wherein the model is trained to output risk factors, importance values for each of the risk factors, and a readmission risk score.

15. The apparatus of claim 11, wherein the processor is further configured to execute the trained model against the first privacy protected data periodically, and generate a visualization comprising the output of the trained model, the visualization being updated periodically.

* * * * *